United States Patent
Aichele et al.

(10) Patent No.: US 9,637,418 B2
(45) Date of Patent: May 2, 2017

(54) METHOD FOR PREPARING AN ESTER AND BINDER SYSTEM

(75) Inventors: Wilfried Aichele, Winnenden (DE); Jochen Rager, Bisingen (DE); Klaus Czerwinski, Heimsheim (DE); Eberhard Grath, Immenstadt (DE); Josef Arnold, Immenstadt (DE); Eva Weisser, Waiblingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 457 days.

(21) Appl. No.: 12/998,875

(22) PCT Filed: Nov. 25, 2009

(86) PCT No.: PCT/EP2009/065834
§ 371 (c)(1),
(2), (4) Date: Aug. 23, 2011

(87) PCT Pub. No.: WO2010/072503
PCT Pub. Date: Jul. 1, 2010

(65) Prior Publication Data
US 2011/0294935 A1    Dec. 1, 2011

(30) Foreign Application Priority Data
Dec. 15, 2008 (DE) .................. 10 2008 054 615

(51) Int. Cl.
| | | |
|---|---|---|
| *B60C 1/00* | (2006.01) | |
| *C04B 35/634* | (2006.01) | |
| *C08K 5/134* | (2006.01) | |
| *B22F 3/22* | (2006.01) | |
| *C04B 35/111* | (2006.01) | |
| *C04B 35/465* | (2006.01) | |
| *C04B 35/484* | (2006.01) | |
| *C04B 35/486* | (2006.01) | |
| *C04B 35/632* | (2006.01) | |
| *C07C 67/03* | (2006.01) | |
| *B22F 1/00* | (2006.01) | |

(52) U.S. Cl.
CPC ........ *C04B 35/63424* (2013.01); *B22F 3/225* (2013.01); *C04B 35/111* (2013.01); *C04B 35/465* (2013.01); *C04B 35/484* (2013.01); *C04B 35/486* (2013.01); *C04B 35/632* (2013.01); *C07C 67/03* (2013.01); *C08K 5/134* (2013.01); B22F 2001/0066 (2013.01); C04B 2235/6022 (2013.01)

(58) Field of Classification Search
CPC ..................................... C08K 5/134
USPC ...................................... 524/287
See application file for complete search history.

(56) References Cited

U.S. PATENT DOCUMENTS

| | | | |
|---|---|---|---|
| 2,062,950 A | 12/1936 | Thomas | |
| 4,309,564 A * | 1/1982 | Loncrini et al. | ................ 560/67 |
| 4,536,593 A | 8/1985 | Orban et al. | |
| 5,002,988 A | 3/1991 | Ono et al. | |
| 5,081,280 A | 1/1992 | Takee et al. | |
| 5,283,213 A * | 2/1994 | Ohst et al. | ................... 264/645 |
| 6,218,567 B1 * | 4/2001 | Koehler et al. | ................ 560/64 |
| 6,348,563 B1 * | 2/2002 | Fukuda et al. | ................ 528/310 |
| 2003/0191217 A1 | 10/2003 | Malz et al. | |
| 2006/0058547 A1 * | 3/2006 | Uehara et al. | ................ 560/128 |

FOREIGN PATENT DOCUMENTS

| | | | |
|---|---|---|---|
| DE | 41 29 952 | 3/1993 | |
| DE | 19942541 A1 * | 3/2001 | ............ C07C 67/02 |
| EP | 0 809 556 | 12/1997 | |
| JP | 59-80636 | 5/1984 | |
| JP | 62-72651 | 4/1987 | |
| JP | 1-301651 | 12/1989 | |
| JP | 5-306162 | 11/1993 | |
| JP | 11-92657 | 4/1999 | |
| JP | 11-310549 | 11/1999 | |
| JP | 2002-309082 | 10/2002 | |
| JP | 2006-124336 | 5/2006 | |
| WO | WO 98/38152 | 3/1998 | |

OTHER PUBLICATIONS

English translation of DE 19942541 A1 to Falkowski et al., Sep. 2006.*
Database CA [Online] Chemical Abstracts Service, Columbus, Ohio,US; 1968, Ozcan, Yildiz: "The C1-22 alkyl salicylates" XP 002568258 & Ozcan, Yildiz: "The C1-22 alkyl salicylates" Istanbul Universitesi Fen Fakultesi Mecmuasi, Seri C: [Astronomi-Fizik-Kimya], 31(1-4), 89-93 Coden: IFMCAL; ISSN: 0444-7298, 1966.
Database CA [Online] Chemical Abstracts Service, Columbus, Ohio, US; 1987, Inoue, Takeshi et al.: "Preparation of docosyl p-hydroxybenzoate as a termite repellent" XP002568259 retrieved from STN Database accession No. 1987.

(Continued)

*Primary Examiner* — Jane L Stanley
(74) *Attorney, Agent, or Firm* — Gerard Messina

(57) ABSTRACT

In a method for preparing an ester from an hydroxybenzoic acid and a fatty alcohol for use in a binder system for powder injection molding, transesterification of an ester of the hydroxybenzoic acid and a low alcohol using the fatty alcohol is carried out, the fatty alcohol and the ester of the hydroxybenzoic acid and the low alcohol forming a reaction mixture and being used in an essentially equimolar ratio. The transesterification is carried out at a temperature at which the ester of the hydroxybenzoic acid and the low alcohol and the fatty alcohol are present as a homogeneous melt. The binder system for a powder injection molding contains 80 to 98 wt. % of a metal powder and/or a ceramic powder and 1 to 19 wt. % of a polymeric binder component, and 1 to 19 wt. % of at least one ester prepared by the transesterification.

10 Claims, No Drawings

(56) References Cited

OTHER PUBLICATIONS

Database CA [Online] Chemical Abstracts Service, Columbus, Ohio, US; 1971, Rodionov, P. P. et al.: "Alkyl salicylates" XP002568260 retrieved from STN Database accession No. 1971: 488267 abstract & Rodionov, P. P. et al.,: "Alkyl salicylates" Metody Polucheniya Khimicheskikh Reaktivov I Preparatov, No. 18, 236-40 From: Ref. Zh., Khim. 1970, Abstr. No. 10ZH257 Coden: MPRPAT; ISSN: 0539-5143, 1969.
Chien-Tien Chen, Jen-Huang Kuo, Cheng-Hsiu Ku, Shiue-Shien Weng, and Cheng-yuan Liu: "Nucleophilic Acyl Substitutions of Esters with Protic Nucleophiles Mediated by Amphoteric, Oxotitanium, and Vanadyl Species" Journal of Organic Chemistry, vol. 70, No. 4, Jan. 22, 2005, pp. 1328-1339, XP002568261 American Chemical Society. Easton, US.
Chen, T. et al., "Nucleophilic acyl substitutions of esters with protic nucleophiles mediated by amphoteric, oxotitanium, and vanadyl species", Journal of Organic Chemistry, Bd. 70, No. 4, Jan. 2005, pp. 1328-1339.
Rodionov et al. "Alkyl salicylates", Metody Polucheniya Khimicheskikh Reaktivov, 1969, No. 18, pp. 236-240, abstract.
Heydt, et al. "Fettalkohole" ("Fatty alcohols"), RÖMPP Online: http://roempp.com/roempp.php, Version 3.19 (2011), pp. 1-4.
LOXIOL® 2472, Emery Oleochemicals, http://shtchem.img6kr/data/LOXIOL 2472.pdf (2006).

\* cited by examiner

METHOD FOR PREPARING AN ESTER AND BINDER SYSTEM

BACKGROUND OF THE INVENTION

1. Field of the Invention

The present invention relates to a method for preparing an ester from a hydroxybenzoic acid and a fatty alcohol for use in a binder system for powder injection molding, as well as a binder system for an injection molding method.

2. Description of Related Art

Binder systems, which are used in powder injection molding, generally contain a polymeric binder component, an additional binder component, a so-called co-binder, which is compatible with the polymeric binder component, and, if necessary, a dispersing agent in order to keep metal or ceramic powder particles in dispersion in the molten binder. The compatibility of the additional binder component having the polymeric binder component means that the binder components in the melt form a uniform liquid phase, and that, even in the solid state, a uniform binder phase (solid solution) is present, the further binder component having to be additionally removable from the common solid phase below its melting point, for instance, by extraction, the polymeric binder component not being permitted to form sources or cracks in a major way.

Polyamides are frequently used as polymeric binder components. As suitable co-binders for polyamides, for example, N,N'-diacetylpiperazine is known from published European patent document EP-B 0 809 556 or from U.S. Pat. No. 5,002,988, and alkylphenols from published German patent document DE-C 41 29 952. When alkylphenols are used, these are generally the ones having $C_1$-$C_{20}$ alkyl.

As further suitable co-binders for binder systems having polyamides as the polymeric binder component, a mixture of various compounds is also used, for example, which contains, among other things, esters of p-hydroxybenzoic acid with various fatty alcohols. Such a mixture was obtainable in the trade under the designation Loxiol 2472®, from the firm of Cognis, for example. However, this mixture also contains contamination, such as phenol, for example. Phenol is physiologically graded as toxic, and, at a temperature of 25° C. it already has a vapor pressure of 41 hPa. This may lead to the release of phenol during running operation, and thus to an endangerment of the health of a user. A further disadvantage of a mixture of various compounds is that a non-uniform composition may occur within a packing container. This results, among other things, from the fact that a melt filled into a barrel hardens very slowly from the outer to the inner region, whereupon fractional crystallization of the individual components occurs. This fractional crystallization has the result that the composition of the product depends on from where in the container the product is taken. The changing of the composition, depending on the place of removal, causes the reproducibility of the powder injection molding process chain to suffer in the steps feedstock processing, injection molding and solvent extraction of the co-binder. A further disadvantage is that components of the co-binder in the injection-molded component separate out. Independently of whether these separations are dissolved out during the extraction or not, a pore develops after sintering, at the location of the separation.

Especially in the use of a mixture of various compounds, which contains, among other things, esters of p-hydroxybenzoic acid with various fatty alcohols, it has also been shown that the injection-molded parts tend to stick to the injection-molding tool.

These disadvantages may particularly be attributed to the fact that fatty alcohols are obtained from natural products and generally come as a mixture. In addition, in the known synthetic method for preparing esters from a hydroxybenzoic acid with a fatty alcohol, phenol is created as a byproduct.

BRIEF SUMMARY OF THE INVENTION

In the method according to the present invention, for preparing an ester from hydroxybenzoic acid and a fatty alcohol for use in a binder system for powder injection molding, by transesterification of an ester from hydroxybenzoic acid and a low alcohol, the fatty alcohol and the ester of the hydroxybenzoic acid and the low alcohol form a reaction mixture, the fatty alcohol and the ester of the hydroxybenzoic acid and the low alcohol are used in an essentially equimolar ratio. The transesterification is carried out at a temperature at which the ester of hydroxybenzoic acid and the low alcohol and the fatty alcohol are present as a homogeneous melt.

"Essentially equimolar" within the meaning of the present invention means that the ester of hydroxybenzoic acid and the low alcohol and the fatty alcohol are present at a mole ratio of maximally 40:60, preferably at a mol ratio of maximally 45:55 and particularly at a mol ratio of 48:52, each of the two components, however, preferably the fatty alcohol, being able to be present in excess.

By contrast to reactions of hydroxybenzoic acid with fatty alcohols, the transesterification of esters of hydroxybenzoic acid and low alcohols is able to be carried out with fatty alcohols at lower temperatures. Because of the lower reaction temperatures, it is avoided that the hydroxybenzoic acid decarboxylates to phenol. In this way, the formation of phenol is able to be greatly reduced, or even avoided. Carrying out the reaction at lower temperatures than those of the reaction of a hydroxybenzoic acid with a fatty alcohol may be attributed to the fact that the ester of the hydroxybenzoic acid and a low alcohol form a common liquid phase, already at lower temperatures. The temperature at which, for instance, p-hydroxybenzoic acid ethyl ester forms a homogeneous liquid phase with an equimolar quantity of 1-docosanol, is generally at 100° C. By contrast, a hydroxybenzoic acid with a fatty alcohol forms a homogeneous fluid phase only a temperatures of more than 195° C. However, at these temperatures, the decarboxylation of the p-hydroxybenzoic acid already sets in.

By fatty alcohol, within the meaning of the present invention, one should understand a 1-alkanol having at least 16 C atoms. Fatty alcohols typically used are, for instance, docosanol $C_{22}H_{45}OH$), 1-alcosanol ($C_{20}H_{41}OH$) or 1-octadecanol ($C_{18}H_{37}OH$), as well as mixtures thereof. Fatty alcohols are mostly obtained from natural products such as beeswax. These usually occur as mixtures.

In general, for the synthesis of technical products, such as esters, mixtures of fatty alcohols that come from natural products are used, their composition being variable. In chemical reactions of these fatty alcohol mixtures no pure products are obtained, but rather product mixtures. However, the melt of such a product mixture may solidify in a fractioned manner when cooled, so that the composition of the solid product in the container differs locally. This leads to feedstocks of variable composition and variable properties, which interferes in powder injection molding. In order to avoid such inhomogeneities, it is therefore preferred that the fatty alcohol used for preparing the ester contains at least 90 wt. % of a specific fatty alcohol component. Specific fatty alcohols having different grades of purity are obtainable in the trade.

By the designation "hydroxybenzoic acid", the present invention means o-hydroxybenzoic acid, p-hydroxybenzoic acid or any mixture of o-hydroxybenzoic acid and p-hydroxybenzoic acid. Accordingly, an ester of hydroxybenzoic acid and a low alcohol, or the ester prepared from hydroxybenzoic acid and a fatty alcohol, is an ester of p-hydroxybenzoic acid, an ester of o-hydroxybenzoic acid or a mixture thereof.

By low alcohol a $C_1$-$C_4$ alkanol is meant, according to the present invention. A low alcohol preferably means methanol, ethanol, 1-propanol and 1-butanol. Methanol and ethanol are particularly preferred as low alcohols. The esters of hydroxybenzoic acid and the low alcohol are thus particularly p-hydroxybenzoic acid methyl ester, o-hydroxybenzoic acid methyl ester, p-hydroxybenzoic acid ethyl ester and o-hydroxybenzoic acid ethyl ester. Mixtures of the respective esters may also be used.

In order to increase the degree of transesterification in the preparation of the ester from hydroxybenzoic acid and the fatty alcohol, it is preferred that one remove the low alcohols which split off during the transesterification, by distillation from the reaction equilibrium. Because of the temperatures required for the reaction, the low alcohols generally evaporate as they are liberated, and can thus already be drawn off as steam from the reaction mixture. This has the additional advantage that the low alcohols are not contained as contamination in the product, namely the ester of hydroxybenzoic acid and the fatty alcohol.

DETAILED DESCRIPTION OF THE INVENTION

In one preferred specific embodiment, the transesterification is carried out in the presence of a catalyst. As the catalyst, organometallic compounds containing tin are particularly suitable. By using the catalyst it is avoided that free p-hydroxybenzoic acid or o-hydrobenzoic acid is created as an intermediate product. This is able to exclude the undesired formation of phenol by decarboxylation of the hydroxybenzoic acid.

In a manner quite especially preferred, the organometallic tin-containing catalyst used is dibutyl-tin dilaurate or butyl-tin oxide hydroxide (butylstannonic acid). The quantity of catalyst used, in relation to the mass of the reaction mixture, is preferably in the range of 0.1 to 1 wt. %. Particularly preferred, the quantity of catalyst used, in relation to the mass of the reaction mixture, amounts to 0.2 to 0.5 wt. %.

In order to avoid that the educts, that is, the esters of the hydroxybenzoic acid and the low alcohol and the fatty alcohol or the products, that is, the ester of the hydroxybenzoic acid and the fatty alcohol, oxidize, and in order, further, to remove the low alcohol from the reaction mixture, whereby it is possible to re-ester the ester used of the hydroxybenzoic acid and the low alcohol almost completely to form the ester of hydroxybenzoic acid and the fatty alcohol, in one preferred specific embodiment a protective gas stream is led through the reaction melt which, among other things, discharges the low alcohol formed from the melt. The protective gas stream is preferably led, along with the low alcohol, into a condenser.

As the protective gas, that is led through the reaction mixture, nitrogen, argon and/or carbon dioxide are suitable. Of these, carbon dioxide is especially preferred, since it counteracts the decarboxylation of hydroxybenzoic acids.

If a catalyst is used, it is preferably added portion by portion during the course of the transesterification. A slight introduction of oxygen into the reaction mixture may be connected with the addition of the catalyst. In order to avoid that, because of the introduction of oxygen, educts or products are oxidized, it is preferred that one add a slight quantity of reducing agent to the reaction mixture. The proportion of the reducing agent, in relation to the mass of the reaction mixture, is preferably in the range of 0.01 to 1 wt. %. Hydroquinone, n-t-butylphenol or benzoin are suitable as reducing agents, for example, hydroquinone being particularly suitable, since its brown oxidation products may be removed from a solution of the products in acetone, for example, by activated charcoal.

Because of their low proportion, the reducing agents do not interfere in the product, and are able to be removed by recrystallization of the product, if necessary.

The ester of hydroxybenzoic acid and a fatty alcohol, prepared by the method according to the present invention, is a clear colorless liquid at the reaction temperature, which contains no free phenol. Because of the purity of the fatty alcohol used, i.e. the proportion of a fatty alcohol component of more that 90 wt. %, the esters are combined uniformly to a great extent. No additional purification is required, and no different product fractions form during solidification. If necessary, one may carry out purification of educts, catalysts and reducing agents by recrystallization from a suitable solvent, such as acetone.

The esters of p-hydroxybenzoic acid and o-hydroxybenzoic acid and a fatty alcohol are soluble in acetone up to more than 99% at a temperature of 48° C. Only the catalysts contained in the ester are able to form residues. In addition, one may assume that the esters formed are largely physiologically harmless.

The present invention also relates to a binder system for a powder injection molding method, containing 80 to 98 wt. % of a metal powder and/or a ceramic powder and 1 to 19 wt. % of a polymeric binder component. Furthermore, 1 to 19 wt. % are contained of at least one ester prepared from hydroxybenzoic acid and a fatty alcohol according to the abovementioned method.

Polyamide is generally used as the polymeric binder component in the binder system. Suitable polyamides are, for instance, Copolyamide 612 (prepared from caprolactam and laurinlactam), mixtures of Polyamide 11 and Polyamide 12 or polyether-blockamide (PEBA).

Metal powders usually used for powder injection molding methods are powders which contain only one metal or a mixture of two or more metals, and/or are themselves alloys.

As ceramic powder, for instance, powders of aluminum oxide, zirconium dioxide, silicon nitride or silicon carbide may be used. It is also possible to use mixtures of two or more of the ceramics named. Moreover, it is also possible to use mixtures which contain both metal powders and ceramic powders. It is preferred, however, to use binder systems which contain either metal powder or ceramic powder.

As described above, the hydroxybenzoic acid, from which the ester is prepared, is o-hydroxybenzoic acid or p-hydroxybenzoic acid, or a mixture thereof.

To obtain a homogeneous melt, it is further preferred that the proportion of ester prepared from a specified fatty alcohol component amount to at least 90 wt. %, in relation to the mass of the ester.

The binder system having the ester of hydroxybenzoic acid and a fatty alcohol, prepared by the method according to the present invention, as co-binder, forms a liquid phase with a polyamide as the polymeric binder component, having a common melting point. After solidifying, the common phase of polymeric binder component and co-binder has a high stretchability. An additional advantage of the binder system according to the present invention is that the co-binder is able to be extracted from the solidified common melt, using a suitable solvent, such as acetone, without the remaining polymeric binder component, for instance, the polyamide, swelling substantially or becoming cracked.

The use of esters of hydroxybenzoic acid and fatty alcohols has the further advantage that the esters themselves are dispersing agents, and that thereby metal powder particles and ceramic powder particles are held in dispersion in the melt of polymeric binder components and co-binders, and consequently the addition of additional dispersing agents, such as fatty acids, is not required. The common phase of polymeric binder component and co-binder also has the advantage that the stretchability of the compound is sufficiently great, so that a sprue in the injection molding tool may be implemented, for example, as a tunnel sprue. Moreover, it has been shown that the ester of hydroxybenzoic acid and fatty alcohol, prepared by the method according to the present invention, is not precipitated during solidification in the injection molding tool, and thus pores in the sintered structure are able to be avoided. Also, the co-binder has a wax-like character and it therefore acts as a form-release parting compound, whereby adhesion of the injection-molded components and sprues on the tool are able to be avoided.

What is claimed is:

1. A method for preparing an ester, comprising:
   forming the ester from an hydroxybenzoic acid and a fatty alcohol by transesterification of an ester of the hydroxybenzoic acid and a low alcohol using the fatty alcohol,
   wherein the fatty alcohol is a mixture of two or more 1-alkanols,
   wherein each of the two or more 1-alkanols has a carbon number of at least 16,
   wherein the carbon numbers of at least two of the two or more 1-alkanols differ,
   wherein the fatty alcohol and the ester of the hydroxybenzoic acid and the low alcohol are used in an essentially equimolar ratio and form a reaction mixture, and
   wherein the transesterification is carried out at a temperature below 195° C. at which the ester of the hydroxybenzoic acid and the low alcohol and the fatty alcohol are present as a homogeneous melt.

2. The method as recited in claim 1, wherein each of the two or more 1-alkanols is selected from the group consisting of 1-docosanol, 1-eicosanol, 1-octadecanol.

3. The method as recited in claim 1, wherein the mixture of two or more 1-alkanols contains at least 90 wt. %, in relation to the mass the ester, of a specific 1-alkanol.

4. The method as recited in claim 2, wherein the low alcohol which split off during the transesterification is removed from the reaction mixture by distillation.

5. The method as recited in claim 2, wherein the transesterification is carried out in the presence of a catalyst.

6. The method as recited in claim 5, wherein the catalyst is an organometallic tin-containing compound.

7. The method as recited in claim 6, wherein the organometallic tin-containing compound is selected from the group consisting of dibutyl-tin oxide, dibutyl-tin dilaurate or butyl-tin oxide hydroxide.

8. The method as recited in claim 6, wherein the quantity of catalyst used, in relation to the mass of the reaction mixture, amounts to 0.1 to 1 wt. %.

9. The method as recited in claim 6, wherein a protective gas stream is led through the reaction mixture.

10. The method as recited in claim 6, wherein a reducing agent is added to the reaction mixture.

* * * * *